(12) United States Patent
Bien

(10) Patent No.: US 11,234,595 B2
(45) Date of Patent: Feb. 1, 2022

(54) RESONATOR ASSEMBLY FOR BIOMETRIC SENSING AND BIOSENSOR USING ELECTROMAGNETIC WAVES

(71) Applicant: UNIST (ULSAN NATIONAL INSTITUTE OF SCIENCE AND TECHNOLOGY), Ulsan (KR)

(72) Inventor: Franklin Don Bien, Ulsan (KR)

(73) Assignee: UNIST (Ulsan National Institute of Science and Technology), Ulsan (KR)

( * ) Notice: Subject to any disclaimer, the term of this patent is extended or adjusted under 35 U.S.C. 154(b) by 0 days.

(21) Appl. No.: 17/195,371

(22) Filed: Mar. 8, 2021

(65) Prior Publication Data

US 2021/0186327 A1 Jun. 24, 2021

Related U.S. Application Data

(63) Continuation of application No. PCT/KR2020/006304, filed on May 13, 2020.

(30) Foreign Application Priority Data

Jun. 21, 2019 (KR) .................. 10-2019-0074031
May 4, 2020 (KR) .................. 10-2020-0053397

(51) Int. Cl.
*A61B 5/00* (2006.01)
*A61B 5/155* (2006.01)
(Continued)

(52) U.S. Cl.
CPC .............. *A61B 5/0002* (2013.01); *A61B 5/05* (2013.01); *A61B 5/145* (2013.01); *A61B 5/155* (2013.01)

(58) Field of Classification Search
CPC ....... A61B 5/0002; A61B 5/155; A61B 5/145; A61B 5/05
See application file for complete search history.

(56) References Cited

U.S. PATENT DOCUMENTS 6,341,504 B1 * 1/2002 Istook .................. H05K 1/0283
66/172 E
10,374,285 B2 * 8/2019 Miura ...................... H01Q 1/48
(Continued)

FOREIGN PATENT DOCUMENTS

| KR | 10-1184420 B1 | 9/2012 |
| KR | 10-1952908 B1 | 3/2019 |
| KR | 10-1953293 B1 | 3/2019 |

OTHER PUBLICATIONS

International Search Report dated Aug. 21, 2020, issued in corresponding Application No. PCT/KR2020/006304, filed May 13, 2020, 6 pages.
(Continued)

*Primary Examiner* — Sean P Dougherty
(74) *Attorney, Agent, or Firm* — Christensen O'Connor Johnson Kindness PLLC

(57) ABSTRACT

A bio sensor using electromagnetic waves according to an embodiment may comprise a resonator assembly, a power supply unit, and a processor. The resonator assembly may include at least one feeding line which is disposed along the outer edge of a feeding area and can feed electric power to the feeding area, and a pattern wire which is disposed along a pattern in the feeding area and can receive electric power from the feeding line through capacitive coupling. The power supply unit may supply electric power to the resonator assembly. While a frequency of the electric power is swept, the processor may acquire a parameter which is biometric data corresponding to a concentration of a target analyte existing around the resonator assembly and is related to a resonant frequency of the resonator assembly.

16 Claims, 20 Drawing Sheets

(51) Int. Cl.
*A61B 5/145* (2006.01)
*A61B 5/05* (2021.01)

(56) References Cited

U.S. PATENT DOCUMENTS

| | | | | |
|---|---|---|---|---|
| 10,849,781 | B2* | 12/2020 | Hansen | G01N 27/041 |
| 2004/0069948 | A1* | 4/2004 | Feisst | B82Y 20/00 |
| | | | | 250/343 |
| 2005/0106713 | A1* | 5/2005 | Phan | A61B 5/150022 |
| | | | | 435/287.2 |
| 2007/0285225 | A1* | 12/2007 | Koyama | G06K 19/07745 |
| | | | | 340/539.12 |
| 2008/0021436 | A1* | 1/2008 | Wolpert | A61M 5/1723 |
| | | | | 604/504 |
| 2009/0143725 | A1* | 6/2009 | Peyser | A61B 5/14865 |
| | | | | 604/66 |
| 2011/0004276 | A1* | 1/2011 | Blair | A61B 90/90 |
| | | | | 607/60 |
| 2012/0223869 | A1* | 9/2012 | Kim | H01Q 5/314 |
| | | | | 343/769 |
| 2012/0246795 | A1* | 10/2012 | Scheffler | A41D 13/0007 |
| | | | | 2/69 |
| 2012/0293385 | A1 | 11/2012 | Liu et al. | |
| 2013/0211208 | A1* | 8/2013 | Varadan | A61B 5/14552 |
| | | | | 600/301 |
| 2014/0187977 | A1 | 7/2014 | Lading | |
| 2014/0266939 | A1* | 9/2014 | Baringer | A61B 5/02416 |
| | | | | 343/729 |
| 2015/0200461 | A1* | 7/2015 | Matsumura | H01Q 13/206 |
| | | | | 343/843 |
| 2021/0121091 | A1* | 4/2021 | Doodeman | A61B 5/05 |
| 2021/0186327 | A1* | 6/2021 | Bien | A61B 5/0002 |

OTHER PUBLICATIONS

Office Action dated Jun. 28, 2021, issued in corresponding Korean Application No. 10-2020-0053397, 6 pages.

* cited by examiner

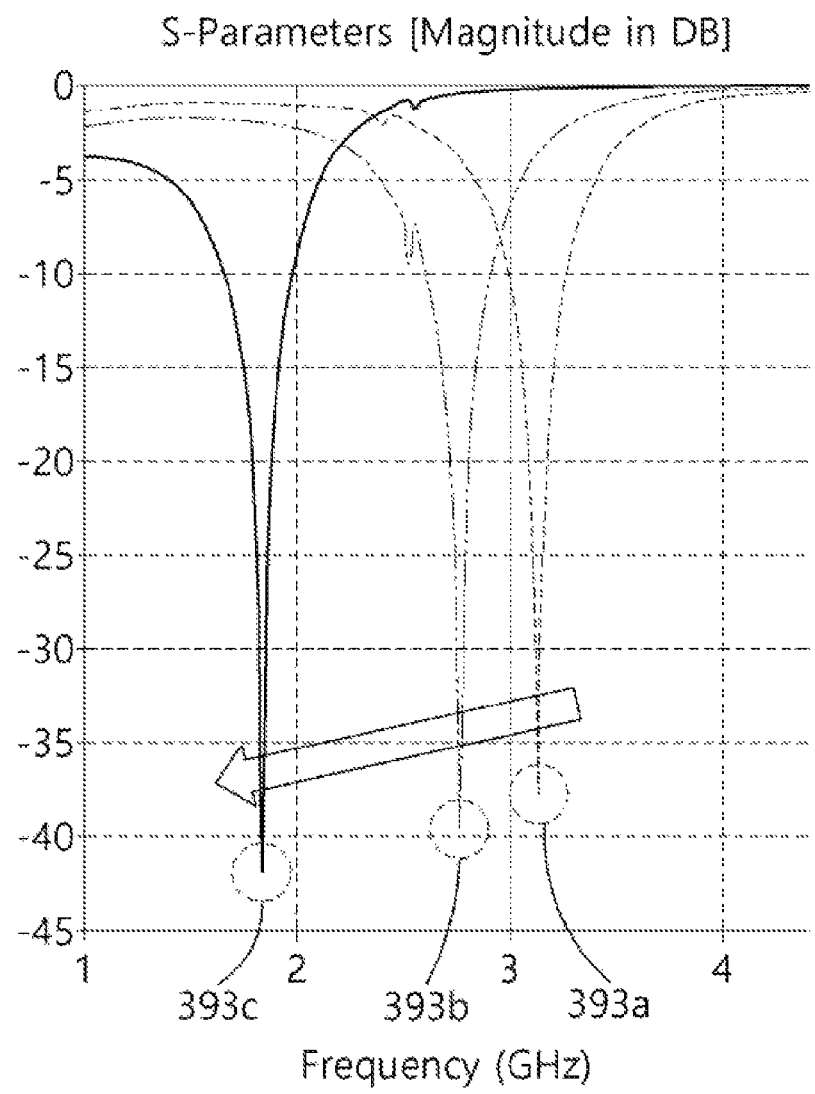

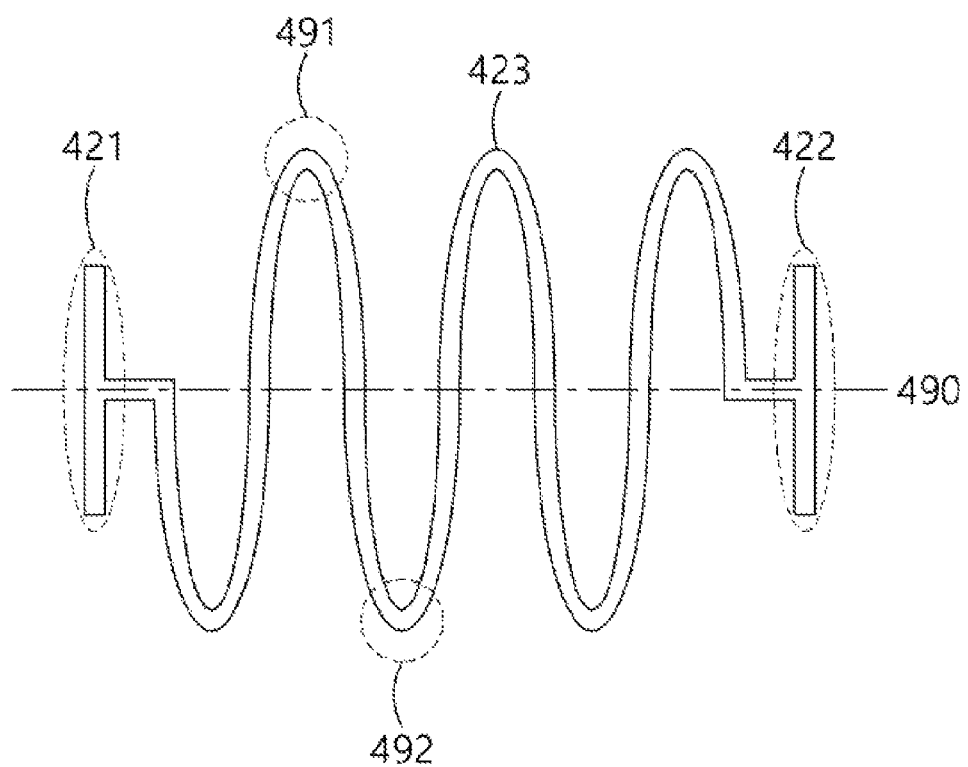

RESONATOR ASSEMBLY FOR BIOMETRIC SENSING AND BIOSENSOR USING ELECTROMAGNETIC WAVES

CROSS-REFERENCES TO RELATED APPLICATIONS

This is a continuation of International Application No. PCT/KR2020/006304, filed May 13, 2020, which claims the benefits of Korean Patent Application No. 10-2019-0074031, filed Jun. 21, 2019, and Korean Patent Application No. 10-2020-0053397, filed May 4, 2020, the disclosures of which are each expressly incorporated herein by reference in their entirety.

BACKGROUND OF INVENTION

Field of Invention

Hereinafter, there are provided a resonator assembly for biometric sensing and a bio sensor using electromagnetic waves.

Description of Related Art

Recently, modern people who suffer from so-called adult diseases, such as diabetes, hyperlipidemia, and thrombophilic patients, are increasing due to the westernization of eating habits. A simple method of checking the relative seriousness of such adult diseases is to measure biometric components within blood. The measurement of the biometric components has an advantage in that whether a numeral value of a specific component is in a normal area or an abnormal area can be easily determined although an ordinary person does not visit a hospital because the amount of several components included in blood, such as blood glucose, anemia, and blood coagulation, can be checked.

One of the easiest methods of measuring biometric components is to inject blood, gathered from the end of a finger, into a test stripe and to quantitatively analyze an output signal using an electrochemical or spectrophotometry method. Such a method is suitable for an ordinal person who does not have expert knowledge because the amount of a corresponding component can be displayed on a measurement unit.

A bio sensor may be coupled to and used with a smart device. There is a need for a technology for accurately determining whether an error is included in data sensed by the bio sensor.

BRIEF SUMMARY OF THE INVENTION

A bio sensor according to an embodiment may sense a concentration of a target analyte using electromagnetic waves.

A bio sensor according to an embodiment may sense a concentration of a target analyte using a meta surface.

A bio sensor according to an embodiment may sense a concentration of a target analyte using relative dielectric constant.

A resonator assembly according to an embodiment may include at least one feeding line disposed on one surface along outskirts of a feeding area and capable of supplying power to the feeding area, and a pattern wire disposed on the one surface along a pattern within the feeding area and capable of receiving power from the feeding line through capacitive coupling.

A resonant frequency of the resonator assembly may be different depending on a concentration of a target analyte present around the resonator assembly.

The resonator assembly further includes a closed-loop wire disposed within the feeding area on the one surface, wherein the pattern wire may be disposed in an internal area defined by a closed-loop wire and forms capacitive coupling with the feeding line via the closed-loop wire.

A part adjacent to a part of the feeding line in the closed-loop wire may be isolated from a part of the feeding line and disposed in parallel to the part of the feeding line in a shape identical with a shape of the part of the feeding line.

The closed-loop wire may be one shape of a polygon or a circular shape.

The pattern wire may include a first coupling portion disposed adjacent to the at least one feeding line on the one surface to form capacitive coupling, a second coupling portion disposed adjacent to at least one of the feeding line, the closed-loop wire, and an additional pattern wire on the one surface to form capacitive coupling, and a connecting portion connecting the first coupling portion and the second coupling portion along the pattern on the one surface.

The connecting portion may include a first part and a second part disposed on opposite sides in a virtual line which traverses the first coupling portion and the second coupling portion.

The first part and the second part may be alternately disposed from the first coupling portion to the second coupling portion.

The first part and the second part may have a point symmetry shape on the one surface.

The connecting portion may be disposed along the pattern having one shape of a sinusoidal shape, a sawtooth shape, a rectangular shape, and a triangular shape.

The resonator assembly may further include one or more additional pattern wires disposed on the one surface in a way to form capacitive coupling with at least one of the pattern wire and the feeding line.

In the resonator assembly, the pattern wire and the one or more additional pattern wires may form a meta surface (MTS).

The pattern wire and the one or more additional pattern wires may be disposed in a form of patterns having an identical shape.

The resonator assembly may further include a plurality of closed-loop wires individually surrounding the pattern wire and the one or more additional pattern wires, respectively, on the one surface.

The one or more additional pattern wires may be isolated and disposed in one axis based on the pattern wire.

The one surface may be a curved surface disposed on a side of a cylindrical support member.

The at least one feeding line includes a first feeding line disposed on the one surface and including ports connected to another element at both ends thereof and a second feeding line isolated from the first feeding line on the one surface and disposed and including ports connected to another element at both ends thereof, wherein the feeding area may be an area between the first feeding line and the second feeding line.

The at least one feeding line may be composed of a single feeding line including a port which receives power, and the feeding area may be an area surrounded by the single feeding line.

A bio sensor using electromagnetic waves according to an embodiment may include a resonator assembly, including at least one feeding line disposed along outskirts of a feeding area and capable of supplying power to the feeding area and a pattern wire disposed along a pattern within the feeding area and capable of receiving power from the feeding line through capacitive coupling, a power supply unit supplying power to the resonator assembly, and a processor obtaining a parameter associated with a resonant frequency of the resonator assembly as biometric data corresponding to a concentration of a target analyte present around the resonator assembly while a frequency of the power is swept.

The bio sensor according to an embodiment can invasively sense a target analyte without a pair of a user by using electromagnetic waves.

The bio sensor according to an embodiment can accurately sense a concentration of a target analyte with high sensitivity by using a meta surface.

The bio sensor according to an embodiment can determine a concentration of a target analyte with low computational complexity by calculating a resonant frequency because relative dielectric constant corresponds to the concentration of the target analyte.

BRIEF DESCRIPTION OF THE DRAWINGS

FIGS. 2, 3a and 3b illustrate a resonator assembly for a bio sensor using electromagnetic waves according to an embodiment.

FIGS. 4 to 6 illustrate examples of a pattern wire according to an embodiment.

DETAILED DESCRIPTION OF THE INVENTION

Figure 1:
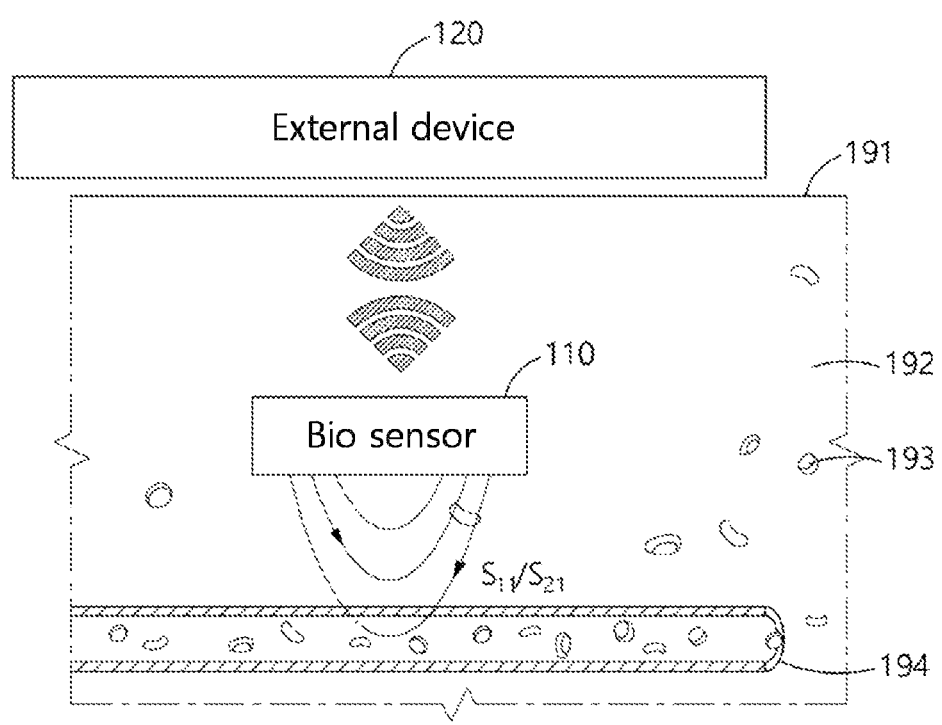
FIG. 1 illustrates a bio sensing system using electromagnetic waves according to an embodiment.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, an element, a part or a combination of them described in the specification, and does not exclude the existence or possible addition of one or more other characteristics, numbers, steps, operations, elements, parts, or combinations of them in advance.

All terms used herein, including technical or scientific terms, have the same meanings as those commonly understood by a person having ordinary skill in the art to which an embodiment pertains, unless defined otherwise in the specification. Terms, such as those commonly used and defined in dictionaries, should be construed as having the same meanings as those in the context of a related technology, and should not be construed as having ideal or excessively formal meanings unless explicitly defined otherwise in the specification.

Furthermore, in describing the present disclosure with reference to the accompanying drawings, the same element is assigned the same reference numeral regardless of its reference numeral, and a redundant description thereof is omitted. In describing an embodiment, a detailed description of a related known art will be omitted if it is deemed to make the gist of the embodiment unnecessarily vague.

Furthermore, in describing elements of an embodiments, terms, such as a first, a second, A, B, (a), and (b), may be used. Such terms are used only to distinguish one element from the other element, and the essence, order, or sequence of a corresponding element is not limited by the terms. When it is said that one element is "connected", "combined", or "coupled" to the other element, the one element may be directly connected or coupled to the other element, but it should also be understood that a third element may be "connected", "combined", or "coupled" between the two elements.

An element included in any one embodiment and an element including a common function are described using the same name in another embodiment. Unless described otherwise, a description written in any one embodiment may be applied to another embodiment, and a detailed description in a redundant range is omitted.

FIG. 1 illustrates a bio sensing system using electromagnetic waves according to an embodiment.

The bio sensing system 100 using electromagnetic waves according to an embodiment may include a bio sensor 110 and an external device 120.

The bio sensor 110 may be a sensor that senses a target analyte 193 by using electromagnetic waves. The target analyte 193 is a material associated with a living body, and may also be indicated as an analyte. For reference, in this specification, the target analyte 193 is chiefly described as blood glucose, but the present disclosure is not limited thereto.

The bio sensor 110 may be inserted and/or implanted into a subcutaneous layer 192 under a skin 191. The bio sensor 110 implanted under the skin may monitor the target analyte 193, present in a blood vessel 194 and the subcutaneous layer 192, by using electromagnetic waves. For example, the bio sensor 110 may measure a parameter associated with a resonant frequency of a resonator assembly to be described later. In this specification, the parameter may indicate a circuit network parameter used to analyze the bio sensor. Hereinafter, a scattering parameter is chiefly described as an example for convenience of description, but the present disclosure is not limited thereto. For example, an admittance parameter, an impedance parameter, a hybrid parameter, and a transmission parameter may be used as the parameter. The resonant frequency of the resonator assembly may be different depending on a concentration of the target analyte 193 present around the resonator assembly. For example, the resonant frequency may be represented as capacitance and inductance of the resonator assembly as in Equation 1 below.

$$f = \frac{1}{2\pi\sqrt{LC}}$$ [Equation 1]

In Equation 1, f may indicate a resonant frequency of the resonator assembly, L may indicate inductance of the resonator assembly, and C may indicate capacitance of the resonator assembly. The capacitance C of the resonator assembly may be proportional to relative dielectric constant $\varepsilon_r$, as in Equation 2.

$$C \propto \varepsilon_r$$ [Equation 2]

The relative dielectric constant of the resonator assembly may be influenced by a concentration of a surrounding target analyte 193. The relative dielectric constant of the resonator assembly is changed in response to a change in the concentration of the target analyte 193, and thus a resonant frequency of the resonator assembly is also changed. Accordingly, the bio sensing system 100 using electromagnetic waves according to an embodiment may determine a concentration of the target analyte 193 based on a resonant frequency of the resonator assembly of the bio sensor 110.

For reference, the resonator assembly according to an embodiment may be designed to sense the target analyte 193. For example, the resonator assembly having a structure to be described later with reference to FIGS. 2 and 3a may have a relatively high Q-factor with respect to a resonant frequency that varies in response a change in the concentration of the target analyte 193. In other words, a frequency response characteristic corresponding to a scattering parameter (hereinafter an "S parameter") of the resonator assembly may indicate a relatively sharp curve within a resonant frequency change range according to a change in the concentration of the target analyte 193. The resonator assembly may indicate high sensitivity with respect to a change in the relative dielectric constant according to a change in the concentration of the target analyte 193. Accordingly, the bio sensor 110 according to an embodiment may accurately determine a resonant frequency of the resonator assembly, and may also accurately estimate a concentration of the target analyte 193 corresponding to the resonant frequency.

For example, if the target analyte 193 is glucose, the resonator assembly may be designed to have specifications, such as Table 1 below. However, the specifications are only illustrative, and the present disclosure is not limited thereto.

TABLE 1

| Parameters | Minimum value | Typical value | Maximum value | Unit | Target material/ target range |
|---|---|---|---|---|---|
| Operating frequency band | 2.0 | 2.45 | 3.0 | GHz | Glucose |
| Resonant peak (S11) (Typical) | | −30 | | dB | Glucose |
| Sensitivity for dielectric constant | | 4 | | MHz | @ per 100 mg/dl |
| Mean Absolute Relative Deviation (MARD) | | | 8.5 | % | |

Figure 2:
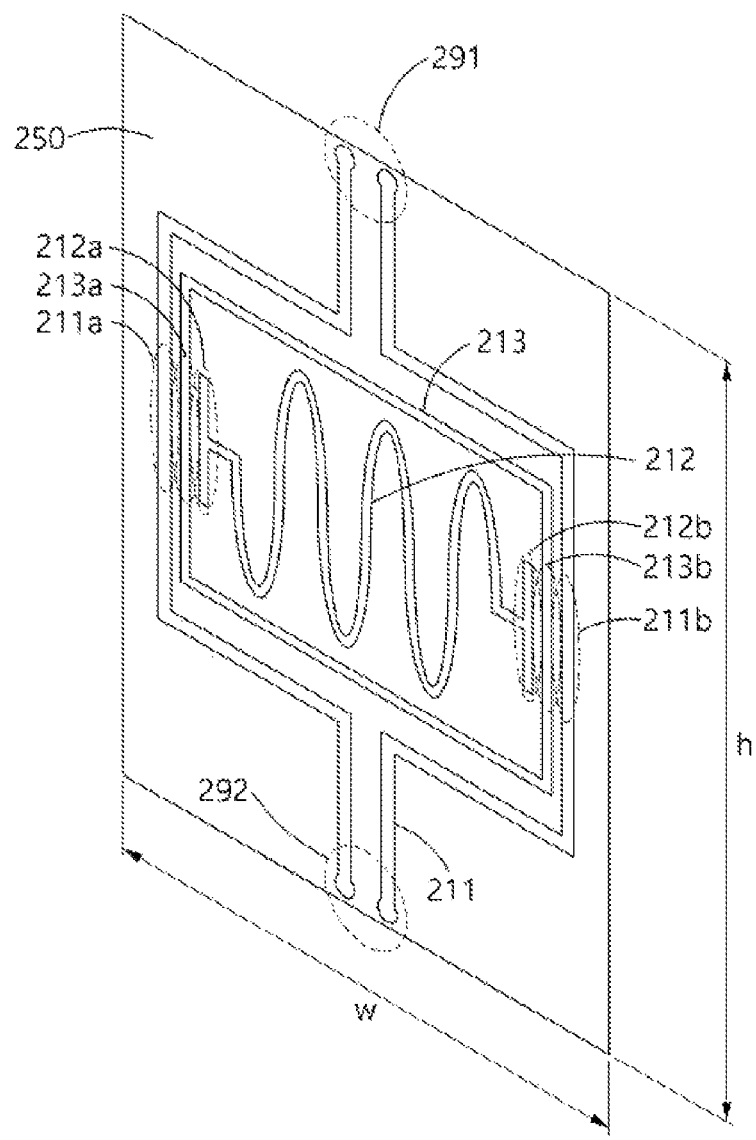
Figure 3A:
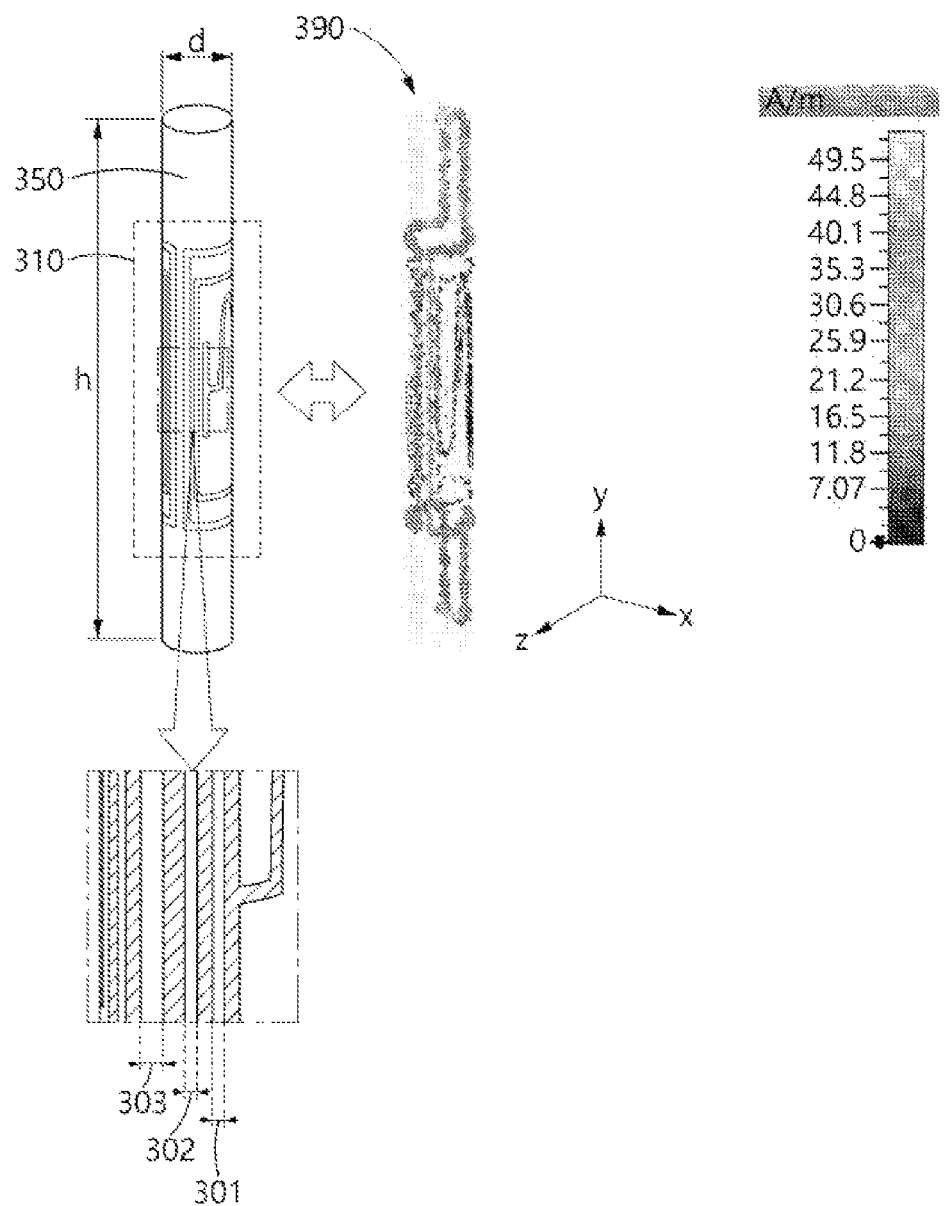

The bio sensor 110 using electromagnetic waves according to an embodiment may wirelessly establish communication with the external device 120. The bio sensor 110 may obtain and collect biometric data corresponding to a concentration of the target analyte 193, and may transmit the biometric data to the external device 120. The biometric data is data related to a concentration and/or amount of the target analyte 193, and may be a parameter associated with a resonant frequency of the resonator assembly as described above, for example, but the present disclosure is not limited thereto. The biometric data may also include a resonant frequency corresponding to a concentration of the target analyte, a scattering parameter for calculating the resonant frequency, a frequency response characteristic corresponding to the scattering parameter, etc. The bio sensor 110 may transmit biometric data to the external device 120 through wireless communication. Moreover, the bio sensor 110 may be wirelessly supplied with power from the external device 120. The bio sensor 110 may monitor biometric data by using wirelessly transmitted power. FIGS. 2, 3a and 3b illustrate a resonator assembly for the bio sensor using electromagnetic waves according to an embodiment.

FIG. 2 illustrates an exemplary resonator assembly 210.

The resonator assembly 210 according to an embodiment may include a feeding line 211, a closed-loop wire 213, and a pattern wire 212.

The feeding line 211 may indicate a conducting wire which is disposed along the outskirts of a feeding area in one surface 250 and can supply power to the feeding area. An area within the feeding line 211 in the one surface 250 may be indicated as the feeding area. The resonator assembly 210 may include at least one feeding line 211. FIG. 2 illustrates an example in which the resonator assembly 210 includes two feeding lines 211. If the feeding lines 211 are 2 in number, an area between the feeding lines 211 may be a feeding area. FIG. 2 illustrates a 2-port structure in which the two feeding lines 211 have a first port 291 on the upper side and a second port 292 on the lower side, but the present disclosure is not limited thereto. An example of a 1-port structure is described with reference to FIG. 14.

The closed-loop wire 213 may be disposed within the feeding area on the one surface 250. The pattern wire 212 to be described may be disposed within an internal area defined by the closed-loop wire 213. The closed-loop wire 213 may be any one shape of a polygon (e.g., a rectangular shape) and a circular shape. FIG. 2 describes an example in which the closed-loop wire 213 has a rectangular shape. The closed-loop wire 213 forms capacitive coupling with the feeding line 211, and may be supplied with power from the feeding line 211. Parts 213a and 213b adjacent to a part of the feeding line 211 in the closed-loop wire 213 may be in parallel isolated and disposed in the same shape as the part of the feeding line 211. The closed-loop wire 213 may provide impedance matching even within a small-sized form factor. Accordingly, if the closed-loop wire 213 is not present, the resonator assembly 210 having the closed-loop wire 213 may indicate a target resonant frequency by using a smaller area than an area necessary to achieve a target resonant frequency (e.g., a resonant frequency corresponding to a target analyte).

The pattern wire 212 is disposed along a pattern within the feeding area in the one surface 250, and may indicate a conducting wire capable of receiving power from the feeding line 211 through capacitive coupling. The pattern wire 212 may indicate an inductance component according to the pattern. The pattern wire 212 may form capacitive coupling with the feeding line 211. For example, parts 212a and 212b of the pattern wire 212 may form capacitive coupling with parts 211a and 211b adjacent thereto, respectively, in the feeding line 211. Furthermore, the pattern wire 212 may form capacitive coupling with the feeding line 211 via the closed-loop wire 213. For example, the parts 212a and 212b of the pattern wire 212 may form capacitive coupling with the parts 213a and 213b adjacent thereto, respectively, in the closed-loop wire 213. Various shapes of the pattern wire 212 are described with reference to FIGS. 4 to 6.

For reference, an exemplary structure of the resonator assembly 210 illustrated in FIG. 2 may be designed to have a height h=26 mm and a width w=14 mm, but the present disclosure is not limited thereto. Furthermore, the one surface 250 on which the resonator assembly 210 illustrated in FIG. 2 is disposed has been illustrated as a plane, but the present disclosure is not limited thereto. FIG. 3a below describes an example in which the resonator assembly 210 is disposed on a curved surface.

FIGS. 3a and 3b describe examples in which one surface along which a resonator assembly is disposed is disposed along the side of a cylinder as a curved surface.

A resonator assembly 310 illustrated in FIG. 3a has the same structure as the resonator assembly 210 illustrated in FIG. 2, and may be disposed along a curved surface 350. A surface current distribution 390 of the resonator assembly 310 is also illustrated. A unit of the surface current distribution 390 is indicated as A/m. In the resonator assembly 310 and the surface current distribution 390, a length axis of the resonator assembly 310 has been illustrated as a y axis. Even in the cylindrical structure, a resonant frequency of the resonator assembly 310 may be changed with high sensitivity in response to a concentration of a surrounding target analyte. The cylindrical resonator assembly 310 illustrated in FIG. 3a has a height h=26 mm and the diameter d=3.96 mm of the cylinder, and may have a smaller form factor than the planar resonator assembly 210 illustrated in FIG. 2.

FIG. 3b illustrates a resonant frequency change and a Q-factor change according to an interval between conducting wires in the resonator assembly 310 illustrated in FIG. 3a.

The resonator assembly 310 may have impedance components (e.g., a resistance component and a capacitance component) by a pattern repeatedly appearing in the pattern wire and the closed-loop wire, and a resonance frequency thereof may be determined by the impedance components. Furthermore, in the resonator assembly 310, if a given one of a plurality of closed-loop wires includes one or more closed-loop wires, a multi-resonance phenomenon may occur.

Capacitance may be increased or decreased by an interval between the pattern wire and the closed-loop wire. Resistance may be increased or decreased by the thickness, width, height, length, etc. of each conducting wire. The Q-factor of the resonator assembly 310 may be determined by capacitance and resistance. A capacitance change according to an interval between the conducting wires and a corresponding resonant frequency change are described.

According to an embodiment, capacitance of the resonator assembly 310 may be different depending on an interval between the conducting wires. For example, in the resonator assembly 310 disposed along the curved surface 350, capacitance of the resonator assembly 310 may be different depending on an interval 303 between a portion corresponding to the length direction (e.g., y-axis direction) of a first feeding line and a portion corresponding to the length direction of a second feeding line (hereinafter an "inter-feeding line interval"). If the inter-feeding line interval 303 is decreased, capacitance of the resonator assembly 310 may be increased. Accordingly, as the inter-feeding line interval 303 is decreased according to Equation 1, a resonant frequency of the resonator assembly 310 may be decreased, and a Q-factor thereof may be increased. In other words, a frequency response characteristic in the resonant frequency of the resonator assembly 310 may become sharp. Illustratively, FIG. 3b illustrates a first resonance point 393a according to a frequency response characteristic when the inter-feeding line interval 303 is a first interval, a second resonance point 393b according to a frequency response characteristic when the inter-feeding line interval 303 is a second interval, and a third resonance point 393c according to a frequency response characteristic when the inter-feeding line interval 303 is a third interval. The third interval may be narrower than the second interval, and the second interval may be narrower than the first interval. A resonant frequency at the third resonance point 393c may be lower than a resonant frequency at the second resonance point 393b, and a resonant frequency at the second resonance point 393b may be lower than a resonant frequency at the first resonance point 393a. Moreover, a degree of attenuation at each resonance point is increased from the first resonance point 393a to the third resonance point 393c. It is illustrated that the Q-factor is increased by a decrease in the interval. In contrast, the resonant frequency of the resonator assembly 310 may be increased and the Q-factor thereof may be decreased by an increase in the inter-feeding line interval 303.

Changes in the resonant frequency and the Q-factor according to the intervals between the feeding lines have been chiefly described with reference to FIG. 3b. The resonant frequency and the Q-factor may be different depending on an interval between other conducting wires. For example, the resonant frequency and the Q-factor may be different depending on an interval 301 between the pattern wire and the closed-loop wire and an interval 302 between the feeding line and the closed-loop wire. The resonator assembly 310 having decreased intervals 301, 302, and 303 may indicate a decreased resonant frequency and an increased Q-factor. In contrast, the resonator assembly 310 having increased intervals 301, 302, and 303 may indicate an increased resonant frequency and a decreased Q-factor.

Moreover, a change in the resonant frequency according to an interval between conducting wires of the cylindrical resonator assembly 310 illustrated in FIG. 3a has been described, but the present disclosure is not limited thereto. Even in the resonator assembly 210 illustrated in FIG. 2, a resonant frequency may be changed depending on an interval between conducting wires as in the cylindrical resonator assembly 310.

Figure 5:
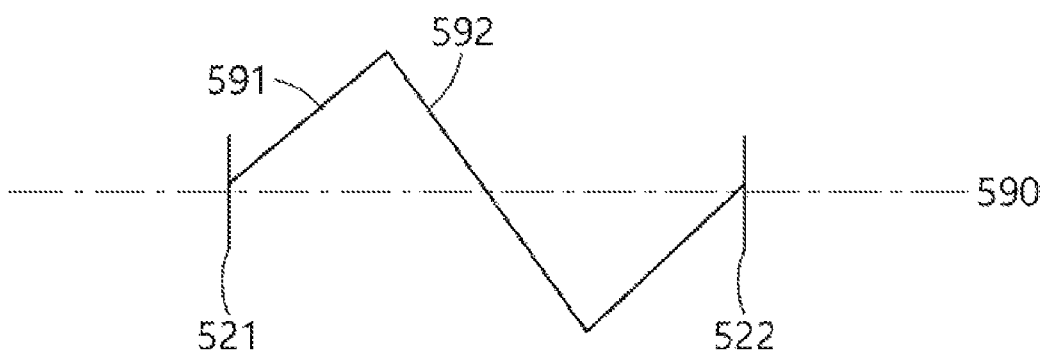
Figure 6:
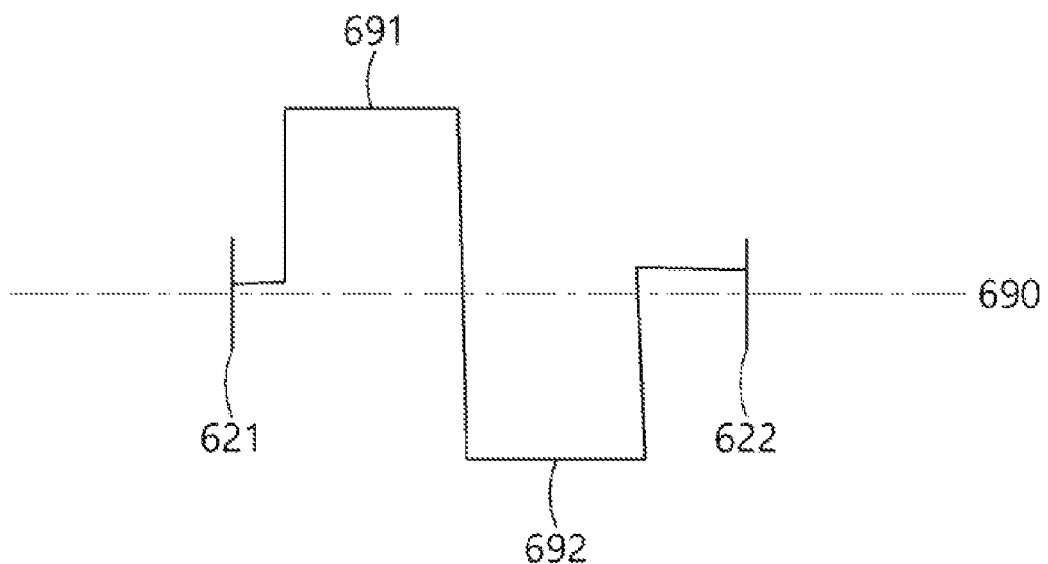

FIGS. 4 to 6 illustrate examples of a pattern wire according to an embodiment.

FIG. 4 describes a pattern wire 420 having a pattern having a sinusoidal shape.

The pattern wire 420 may include a first coupling portion 421, a second coupling portion 422, and a connecting portion 423.

The first coupling portion 421 and the second coupling portion 422 may indicate portions that form capacitive coupling with other conducting wires in the pattern wire 420. For example, the first coupling portion 421 is disposed adjacent to at least one feeding line in one surface, and may form capacitive coupling. The second coupling portion 422 is disposed adjacent to at least one of a feeding line, a closed-loop wire, and an additional pattern wire in the one surface, and may form capacitive coupling. The additional pattern wire is an additionally disposed pattern wire in addition to a basic pattern wire, and is described with reference to FIGS. 9 to 11. A first coupling portion and second coupling portion of the additional pattern wire may form capacitive coupling with another pattern wire.

For example, the first coupling portion 421 may have the same shape as a part adjacent to the first coupling portion 421 in the feeding line, and may be isolated from the adjacent part in parallel. For another example, if the pattern wire is disposed in an area within the closed-loop wire, the first coupling portion 421 may have the same shape as a part adjacent to the first coupling portion 421 within the closed-loop wire, and may be isolated from the adjacent part in parallel. The second coupling portion 422 may have the same shape as a part adjacent to the second coupling portion 422 in an adjacently disposed conducting wire among the feeding line, the closed-loop wire, and the additional pattern wire, and may be isolated from the adjacent part in parallel.

The connecting portion 423 may connect the first coupling portion 421 and the second coupling portion 422 along the pattern in the one surface. For example, the connecting portion 423 may include a first part 491 and a second part 492 disposed on opposite sides in a virtual line 490 that traverses the first coupling portion 421 and the second coupling portion 422. The first part 491 and the second part 492 may be alternately disposed from the first coupling portion 421 to the second coupling portion 422. For example, the first part 491 and the second part 492 may have a point symmetry shape on the one surface. The pattern wire 420 illustrated in FIG. 4 has a sinusoidal shape, and each of the first part 491 and the second part 492 may include a curved portion. The resonator assembly may have an inductance component depending on a pattern of the connecting portion 423. In this case, the connecting portion 423 may be isolated from the feeding line, the closed-loop wire, and another pattern wire in order to prevent capacitive coupling with the feeding line, the closed-loop wire, and another pattern wire.

The pattern of the connecting portion 423 is not limited to that illustrated in FIG. 4. The connecting portion 423 may be disposed along a pattern having one of a sinusoidal shape, a sawtooth shape, a rectangular shape, and a triangular shape.

FIG. 5 describes a pattern wire according to a pattern having a triangular shape.

A first coupling portion 521, second coupling portion 522, and virtual line 590 of the pattern wire 520 are the same as those of FIG. 4, and a description thereof is omitted. The pattern wire 520 according to the pattern having the triangular shape may include straight-line portions 591 and 592 that traverse the virtual line 590.

FIG. 6 describes a pattern wire according to a pattern having a rectangular shape.

A first coupling portion 621, second coupling portion 622, and virtual line 690 of the pattern wire 620 are the same as those of FIG. 4, and a description thereof is omitted. The pattern wire 620 according to the pattern having the rectangular shape may include straight-line portions 691 and 692 which are parallel to the virtual line 690 and disposed on opposite sides in the virtual line 690.

FIGS. 7 to 12 illustrate additional examples of resonator assemblies according to an embodiment.

Figure 7:
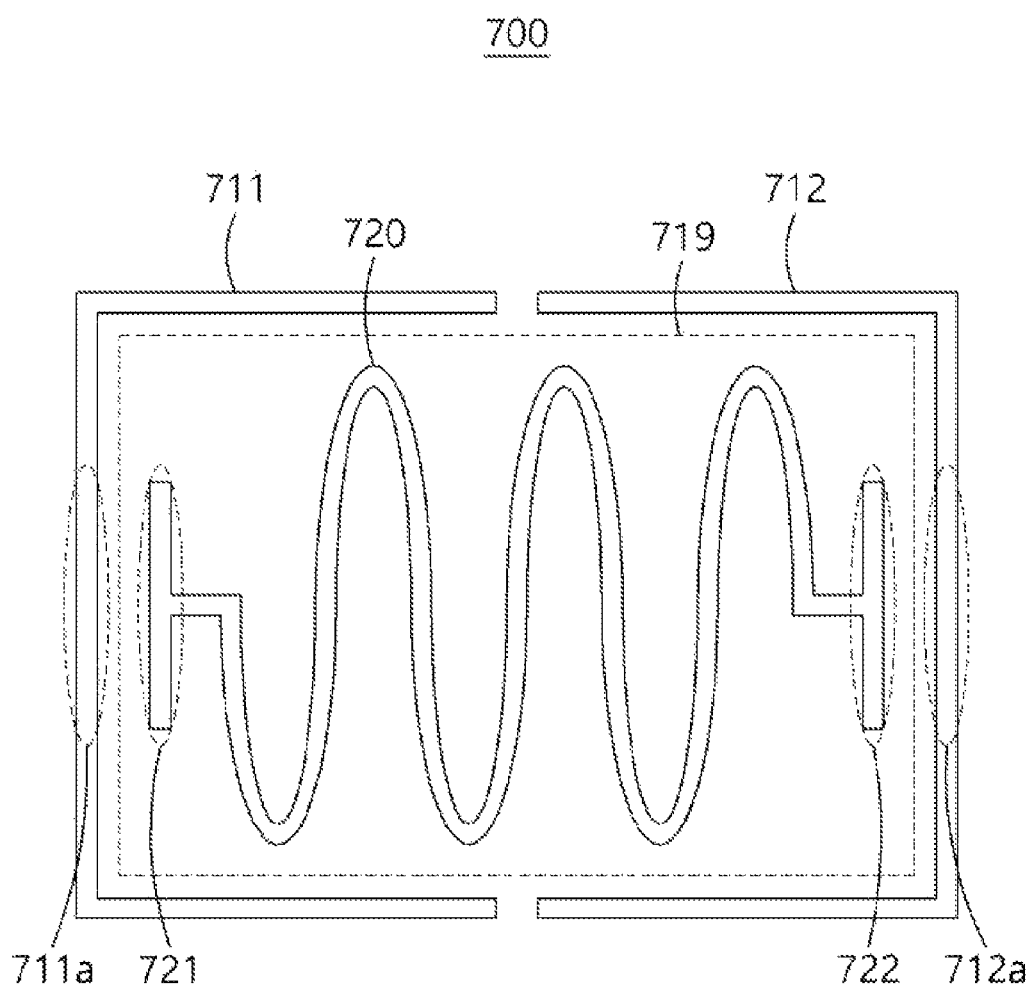
FIGS. 7 to 12 illustrate additional examples of resonator assemblies according to an embodiment.

FIG. 7 describes an example of a resonator assembly not having a closed-loop wire.

The resonator assembly 700 according to an embodiment may include feeding lines and a pattern wire 720 without a closed-loop wire. In FIG. 7, two feeding lines 711 and 712 may define a feeding area 719. Each of the two feeding lines 711 and 712 may be disposed along at least some of the outskirts of the feeding area 719.

Coupling portions 721 and 722 of the pattern wire 720 may form capacitive coupling with the feeding lines. For example, a first coupling portion 721 of the pattern wire 720 may form capacitive coupling with a part 711a of the first feeding line 711. A second coupling portion 722 of the pattern wire 720 may form capacitive coupling with a part 712a of the second feeding line 712. For reference, in FIG. 7, an example of two ports separated into the first feeding line 711 and the second feeding line 712 has been described, but the present disclosure is not limited thereto. The feeding line may be implemented in a single feeding line form instead of the first feeding line 711 and the second feeding line 712.

Figure 8:
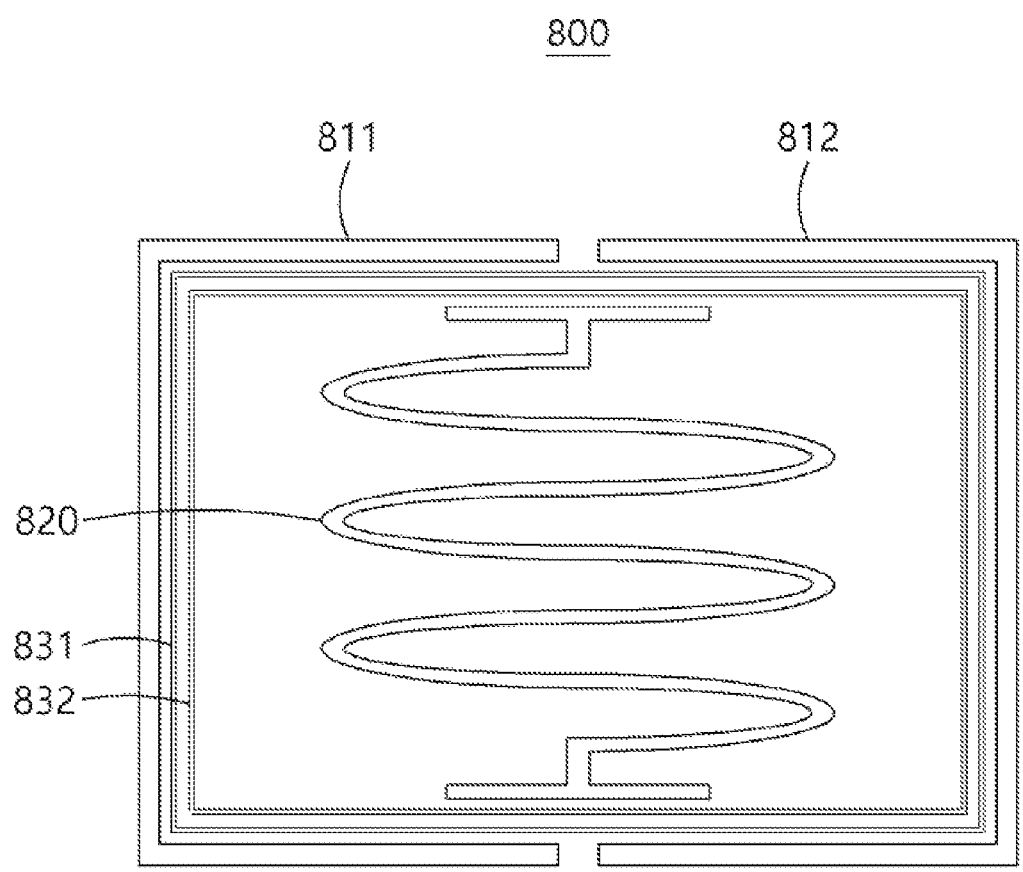

FIG. 8 describes a resonator assembly including a pattern wire and one or more closed-loop wires which are differently arranged.

In the resonator assembly 800 according to an embodiment, a pattern wire 820 may be variously arranged with respect to feeding lines. For example, in FIGS. 1 to 7, the coupling portions of the pattern wire 820 are disposed adjacent to conducting wires between ports of the feeding lines, but the coupling portions of the pattern wire 820 illustrated in FIG. 8 may be disposed adjacent to the ports of the feeding lines.

Furthermore, the resonator assembly 800 may include one or more closed-loop wires. For example, a plurality of closed-loop wires may be disposed within a feeding area defined by feeding lines 811 and 812. At least one of the plurality of closed-loop wires 831 and 832 may be disposed in an internal area defined by another closed-loop wire. For example, in FIG. 8, a first closed-loop wire 831 may be disposed within the feeding area in one surface, and a second closed-loop wire 832 may be disposed in an internal area defined by the first closed-loop wire 831. The pattern wire 820 may be disposed in an internal area defined by the second closed-loop wire 832.

According to an embodiment, a resonator assembly may further include an additional pattern wire. For example, one or more additional pattern wires may be disposed on one surface in a way to form capacitive coupling with at least one of a pattern wire and a feeding line.

Figure 9:
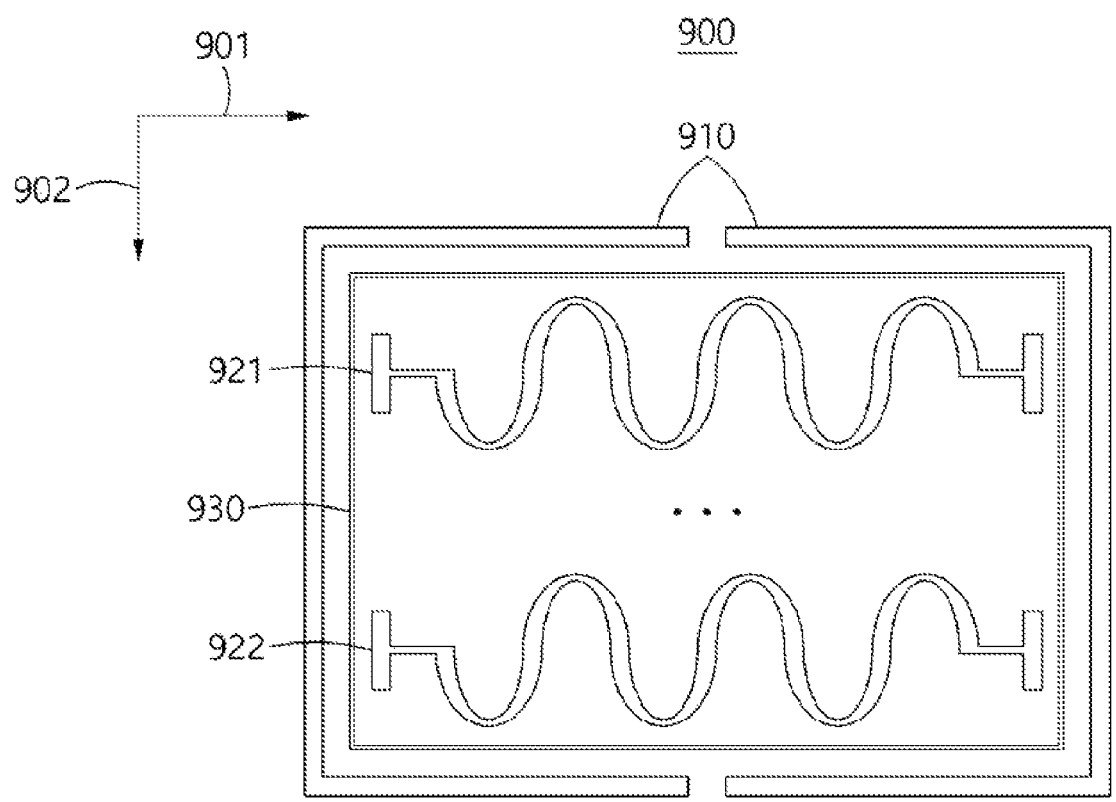

FIG. 9 describes an example in which an additional pattern wire 922 is disposed to form capacitive coupling with feeding lines. A resonator assembly 900 may further include the additional pattern wire 922 in addition to a basic pattern wire 921. The resonator assembly 900 may include a closed-loop wire 930 disposed within a feeding area defined by feeding lines 910. The basic pattern wire 921 and the additional pattern wire 922 may be disposed within an area defined by the closed-loop wire 930. The additional pattern wire 922 and the basic pattern wire 921 may be disposed in parallel. For example, the additional pattern wire 922 may be isolated from the basic pattern wire 921 and disposed in a second axis 902 perpendicular to a first axis 901 that traverses a first coupling portion and second coupling portion of the basic pattern wire 921. Moreover, FIG. 9 illustrates only one additional pattern wire 922, but the present disclosure is not limited thereto. One or more additional pattern wires 922 may be disposed within the feeding area.

Figure 10:
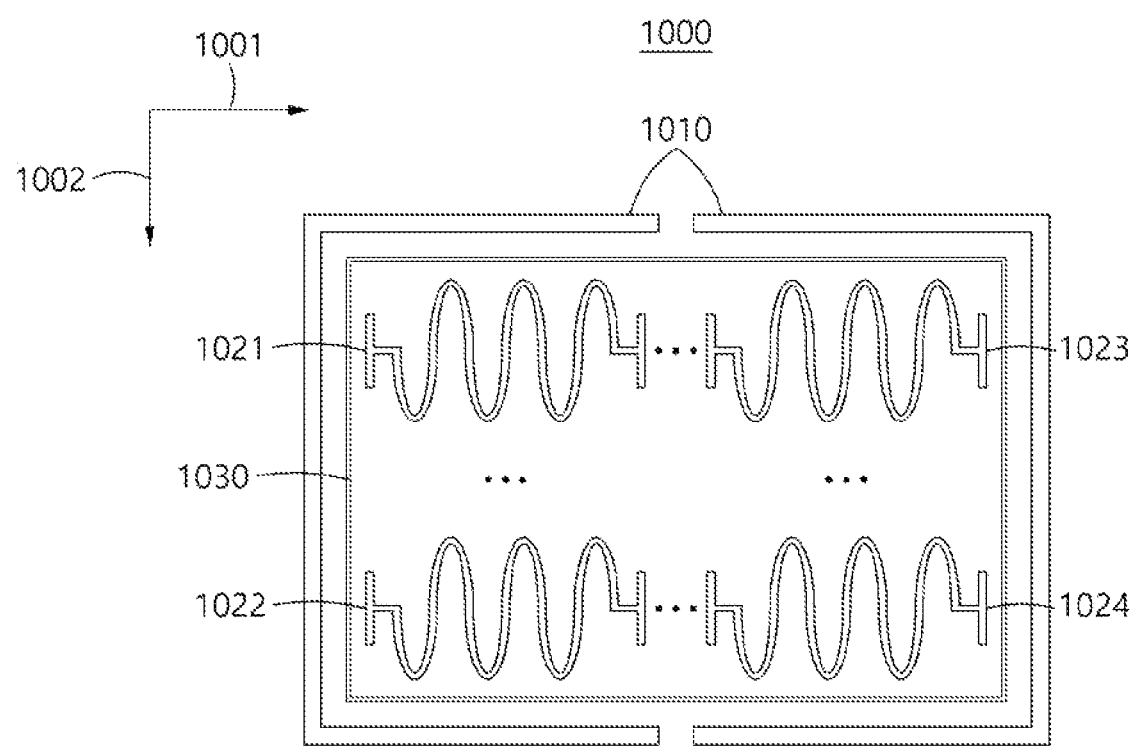

FIG. 10 describes an example of an additional pattern wire that forms capacitive coupling with another pattern wire. For example, a second pattern wire 1022 may be isolated from a first pattern wire 1021 and disposed in a second axis 1002 in one surface. A third pattern wire 1023 may be isolated from the first pattern wire 1021 and disposed in a first axis 1001 in the one surface. A fourth pattern wire 1024 may be isolated from the second pattern wire 1022 and disposed in the first axis 1001. The first pattern wire 1021 and the third pattern wire 1023 may form capacitive coupling directly or via another additional pattern wire. The second pattern wire 1022 and the fourth pattern wire 1024 may form capacitive coupling directly or via another additional pattern wire. FIG. 10 illustrates only the four pattern wires, but the present disclosure is not limited thereto. n pattern wires may be isolated and disposed in the first axis 1001, and m pattern wires may be isolated and disposed in the second axis 1002. Accordingly, the resonator assembly 1000 may include n×m pattern wires. In this case, each of n and m may be an integer of 1 or more.

Moreover, FIG. 10 illustrates only a single closed-loop wire 1030 within an area defined by feeding lines 1010, but the present disclosure is not limited thereto. The resonator assembly 1000 may include one or a plurality of closed-loop wires within the feeding area. Each of the closed-loop wires may include one or a plurality of pattern wires. FIG. 10 describes an example in which each of a plurality of closed-loop wires 1131, 1132, 1133, and 1134 includes a single pattern wire.

Figure 11:
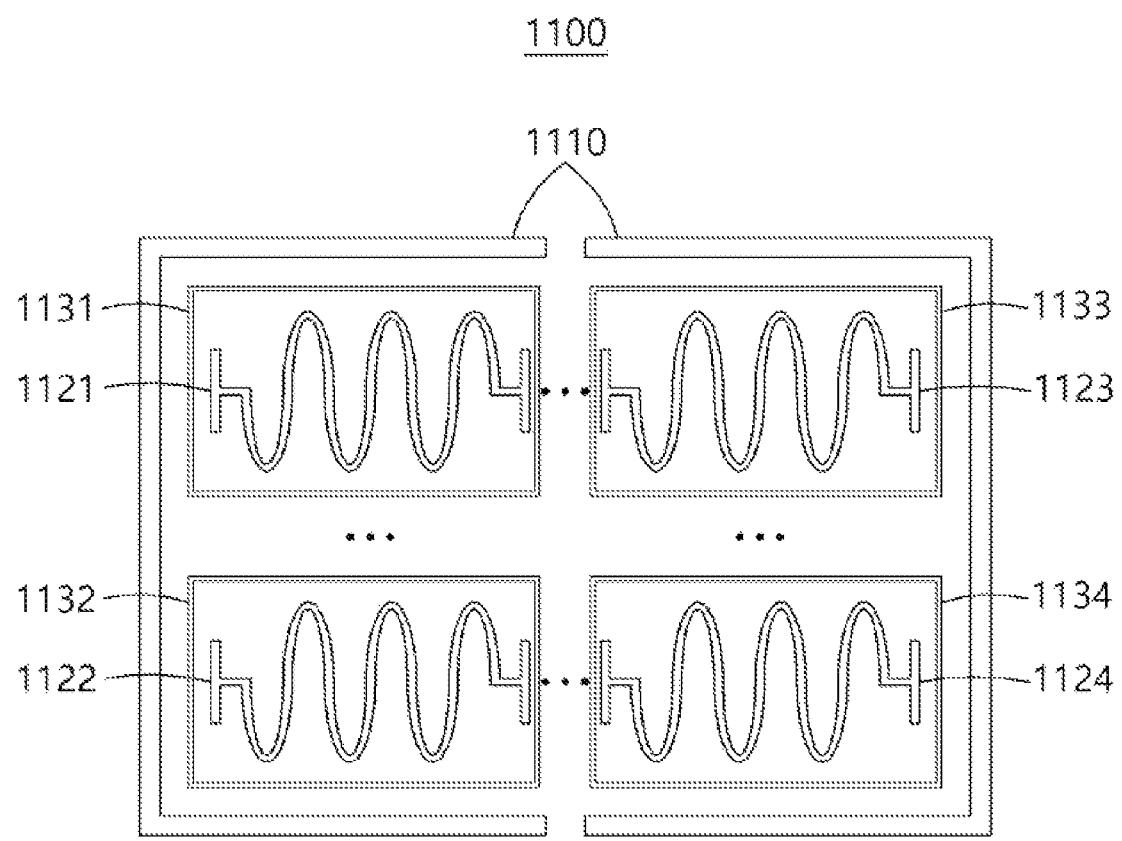

FIG. 11 describes an exemplary structure including the closed-loop wires 1131, 1132, 1133, and 1134 that surround individual pattern wires in the structure illustrated in FIG. 10. According to an embodiment, a resonator assembly 1100 may include a plurality of closed-loop wires 1131, 1132, 1133, and 1134 within a feeding area defined by the feeding line 1110. The plurality of closed-loop wires 1131, 1132, 1133, and 1134 may individually surround a pattern wire 1121 and one or more additional pattern wires 1122, 1123, and 1124, respectively, in one surface.

In FIGS. 10 and 11, the pattern wire and the one or more additional pattern wires may be disposed as patterns having the same form. In this case, the pattern wire and the one or more additional pattern wires may form a meta surface (MTS).

The feeding area having a rectangular shape has been chiefly described above, but the present disclosure is not limited thereto.

Figure 12:
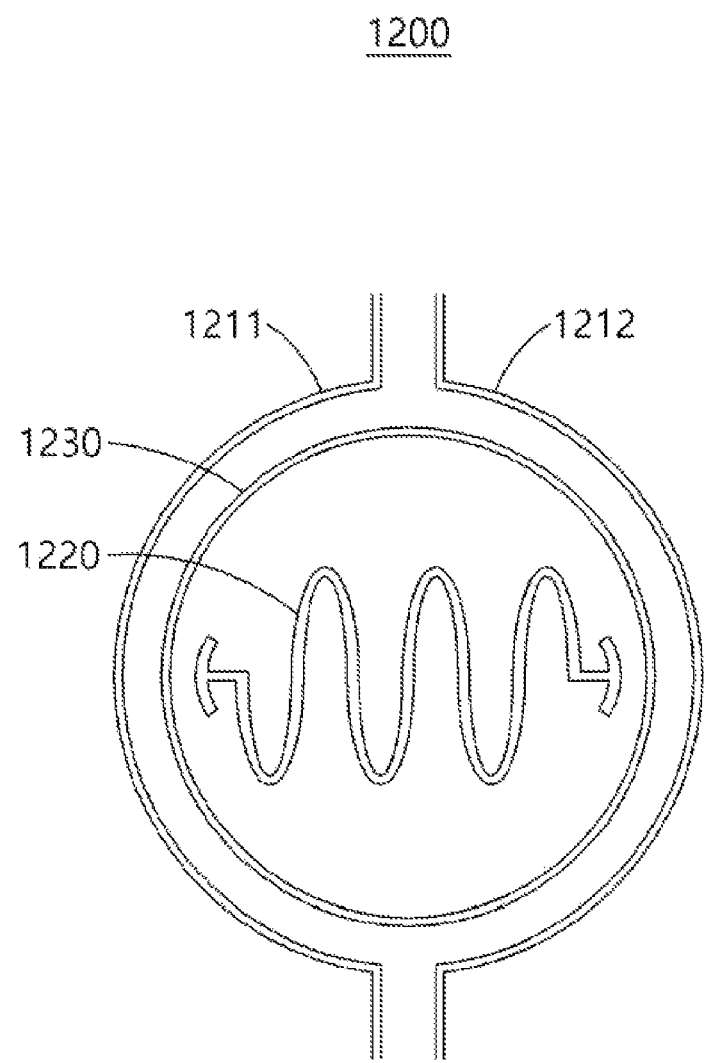

FIG. 12 describes a resonator assembly 1200 having a circular feeding area. Feeding lines 1211 and 1212 may be disposed along the outskirts of a circular feeding area. A closed-loop wire 1230 may be configured in a circular shape in accordance with the shape of the feeding area. A pattern wire 1220 may be disposed within the circular feeding area. In this case, coupling portions of the pattern wire 1220 may be isolated in parallel with respect to the shapes of the feeding lines 1211 and 1212 and the closed-loop wire 1230, and may be configured in a form, that is, a part of a circumference.

Figure 13:
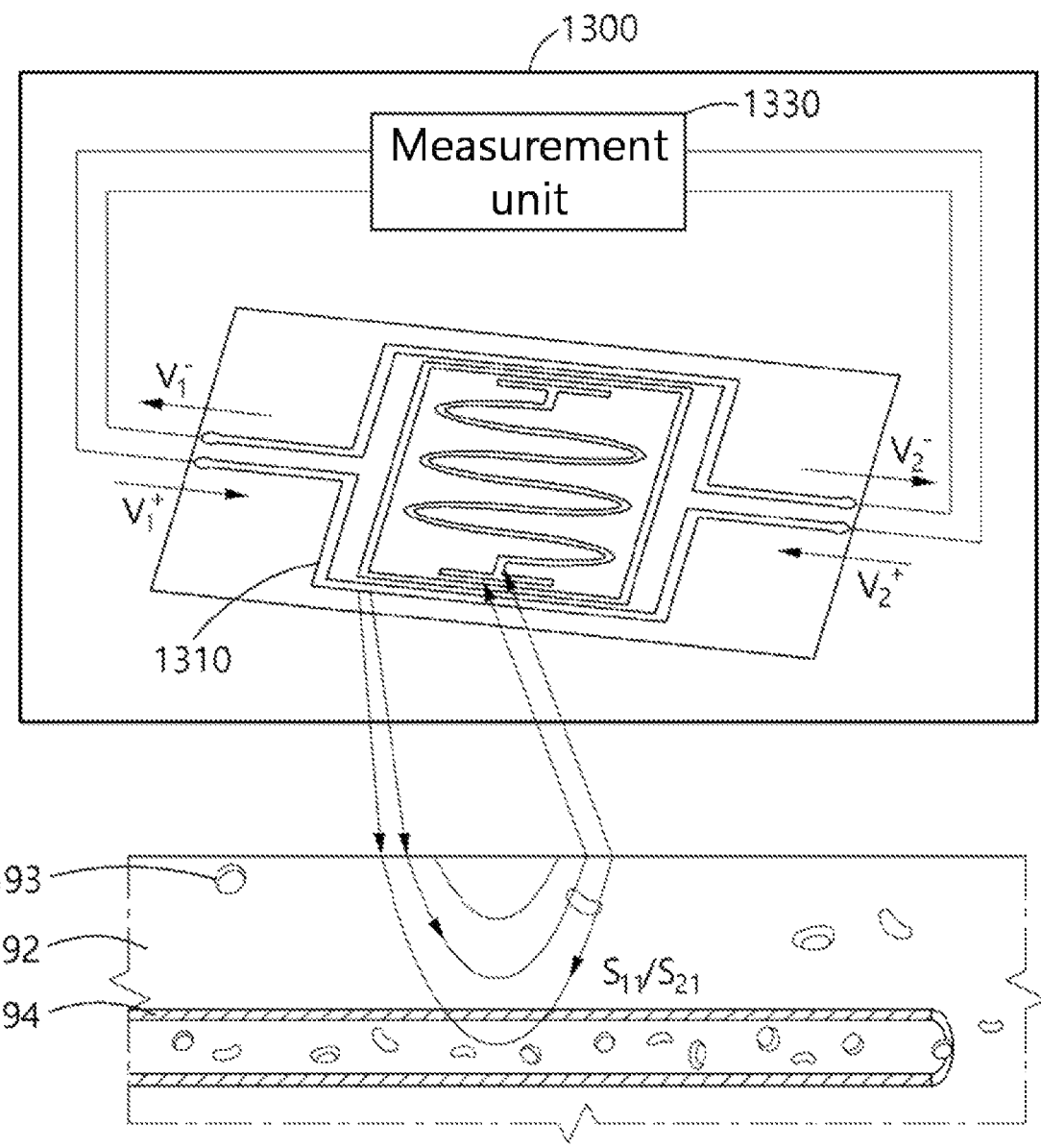
FIG. 13 illustrates an example of two ports of a bio sensor using electromagnetic waves according to an embodiment.

FIG. 13 illustrates an example of two ports of a bio sensor using electromagnetic waves according to an embodiment.

A resonator assembly 1310 according to an embodiment may be implemented using two ports. For example, a first feeding line is disposed on one surface, and may include ports coupled to another element at both ends thereof. A second feeding line is isolated from the first feeding line in the one surface, and may include ports coupled to another element at both ends thereof. A feeding area may be an area between the first feeding line and the second feeding line.

A bio sensor 1300 according to an embodiment may sense biometric data by using the resonator assembly 1310 implemented using the two ports.

A measurement unit 1330 may measure a frequency response characteristic of the resonator assembly 1310 while applying a signal having a frequency to the resonator assembly 1310. For example, the measurement unit 1330 may include an oscillation circuit capable of adjusting an oscillation frequency and a signal detection circuit for detecting a voltage, a current, power, a signal waveform, etc. input to or output by the resonator assembly 1310, but a circuit configuration of the measurement unit 1330 is not limited thereto and may be different depending on the design.

According to an embodiment, the measurement unit 1330 of the bio sensor 1300 may sweep a frequency of power applied to the resonator assembly 1310. The measurement unit 1330 may sweep the frequency of power by changing the frequency within a predetermined target frequency range. The measurement unit 1330 may sequentially increase the frequency of power from the lower limit of the target frequency range to the upper limit thereof or may sequentially decrease the frequency of power from the upper limit of the target frequency range to the lower limit thereof. If a target analyte is blood glucose, the target frequency range is a range including 2.54 GHz, for example, and may be a range from 2 GHz to 3.6 GHz, but the present disclosure is not limited thereto. The target frequency range may be a range including 5.8 GHz. The target frequency range may be differently set depending on the type of target analyte, but this is illustrative. Frequency sweeping is not limited thereto, and various methods may be used.

The measurement unit 1330 of the bio sensor 1300 may measure information (e.g., a frequency response characteristic and a resonant frequency) related to a frequency characteristic of the resonator assembly 1310 while the frequency of power applied to the resonator assembly 1310 is swept. For example, the measurement unit 1330 may measure a voltage ($V_1^+$, $V_1^-$) input to or output by the first port of the resonator assembly 1310 and a voltage ($V_2^+$, $V_2^-$) input to or output by the second port of the resonator assembly 1310 through a voltage sensor. The processor (not illustrated) of the bio sensor 1300 may determine a scattering parameter based on the voltages input to or output by the first port and the second port. The processor (not illustrated) may collect the scattering parameter during the frequency sweeping, and may determine a resonant frequency of the resonator assembly 1310 based on the collected scattering parameter. The scattering parameter may include an $S_{11}$ parameter indicative of a ratio of a voltage input to the first port and a voltage output by the first port and an $S_{21}$ parameter indicative of a ratio of the voltage input to the first port and the voltage output by the second port, for example. A response characteristic corresponding to the scattering parameter is described below with reference to FIGS. 15 and 16.

As described above, relative dielectric constant associated with the resonator assembly 1310 may be changed in a subcutaneous layer 1392 depending on a concentration of a target analyte 1393 included in the blood of a blood vessel 1394. Accordingly, the bio sensor 1300 may estimate a concentration of the target analyte by determining a resonant frequency based on a scattering parameter, but the present disclosure is not limited thereto. The bio sensor 1300 may collect only the scattering parameter as biometric data during frequency sweeping, and may transmit the collected scattering parameter to the external device. At this time, the external device may determine a resonant frequency based on the received scattering parameter, and may determine a concentration of the target analyte corresponding to the resonant frequency.

Figure 14:
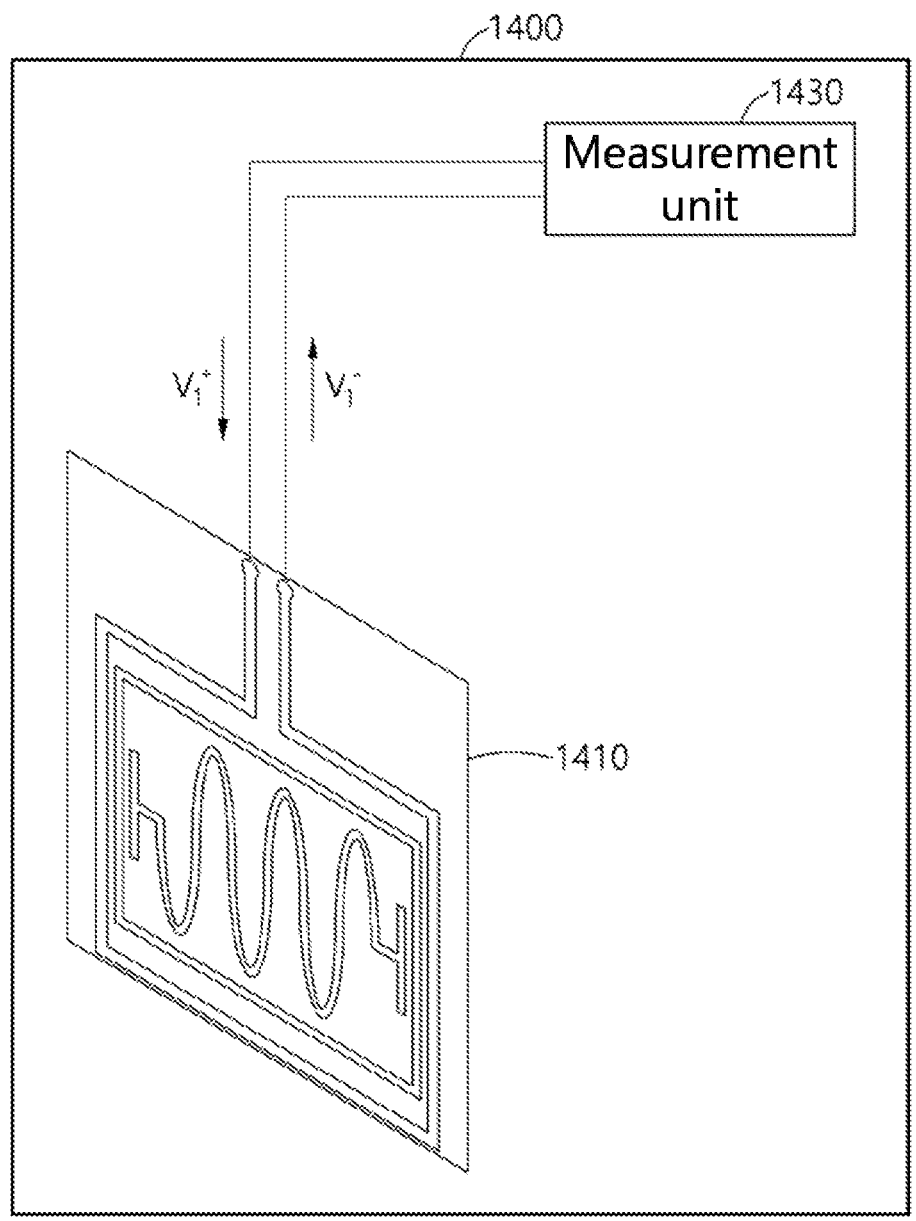
FIG. 14 illustrates an example of one port of a bio sensor using electromagnetic waves according to an embodiment.

FIG. 14 illustrates an example of one port of a bio sensor using electromagnetic waves according to an embodiment.

The resonator assembly 1410 according to an embodiment may be implemented using one port. For example, in the resonator assembly 1410, at least one feeding line may be composed of a single feeding line including a port that receives power. In this case, a feeding area may be an area surrounded by the single feeding line.

While a frequency of power applied from a measurement unit 1430 to the resonator assembly 1410 is swept, the measurement unit 1430 may measure a voltage input to or output by the one port with respect to the resonator assembly 1410 implemented using the one port. A processor may calculate an $S_{11}$ parameter based on the voltage input to or output by the one port. The processor may obtain a frequency response characteristic corresponding to the $S_{11}$ parameter from the measurement unit 1430 during frequency sweeping. The processor may determine a resonant frequency of the resonator assembly 1410 based on the frequency response characteristic. The bio sensor 1400 may output, as biometric data, at least one of a scattering parameter, a frequency response characteristic corresponding to the scattering parameter, a resonant frequency, and a concentration of a target analyte corresponding to the resonant frequency to the external device.

Figure 15:
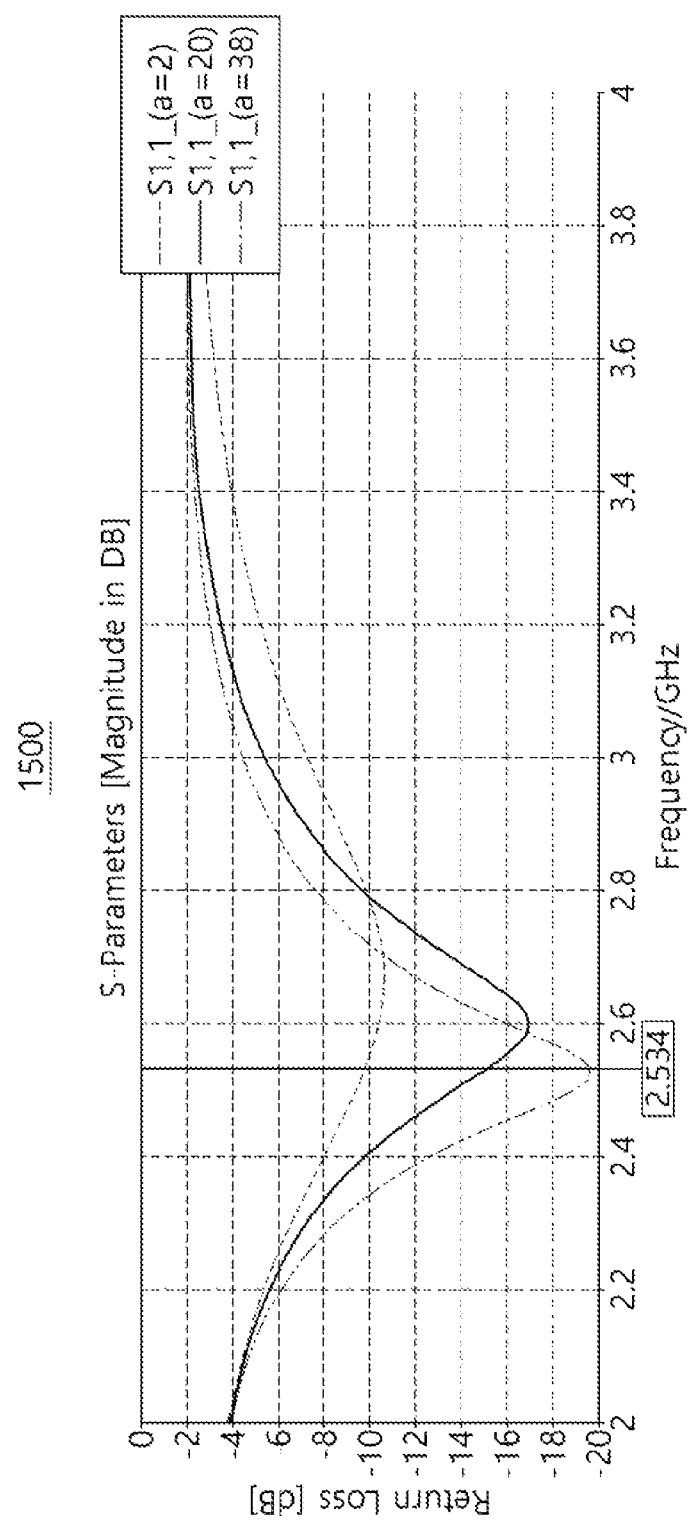
FIGS. 15 to 17 describe relations between a scattering parameter of the bio sensor using electromagnetic waves and a concentration of a target analyte according to an embodiment.
Figure 16:
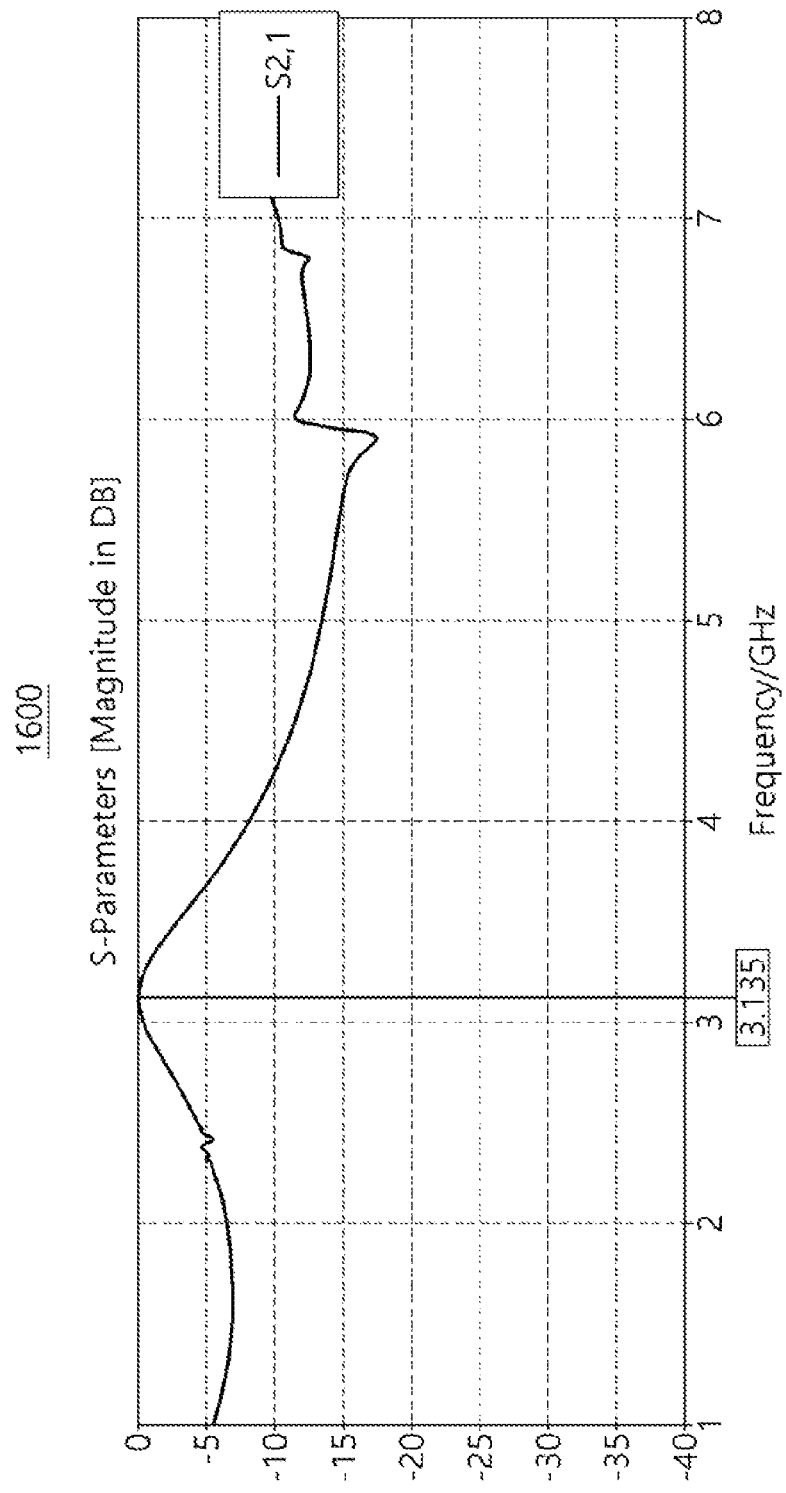
Figure 17:
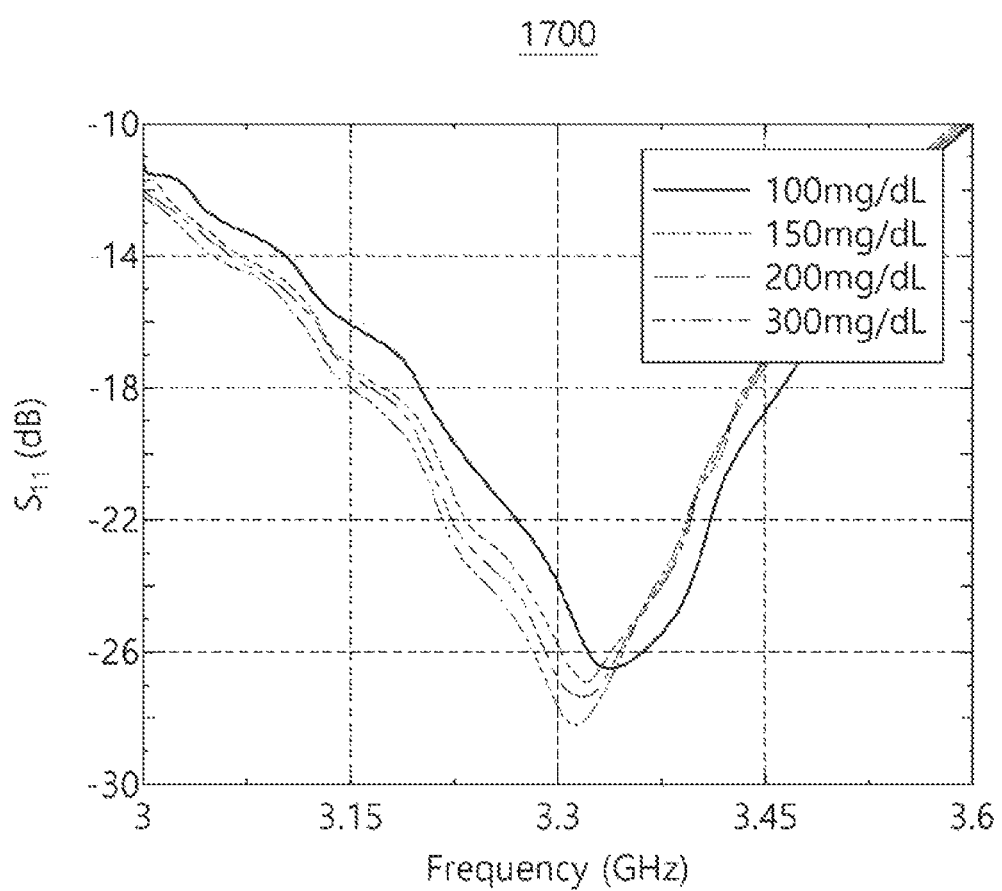

FIGS. 15 to 17 describe relations between a scattering parameter of the bio sensor using electromagnetic waves and a concentration of a target analyte according to an embodiment.

FIG. 15 may indicate a frequency response characteristic curve 1500 of the $S_{11}$ parameter for each relative dielectric constant. In the frequency response characteristic curve 1500, a vertical axis is a return loss [dB], and a horizontal axis is a frequency [GHz]. In the frequency response characteristic curve 1500, a frequency in which the return loss is a minimum may be a resonant frequency. For example, if the bio sensor monitors the $S_{11}$ parameter among scattering parameters, the bio sensor may search a target frequency range for a frequency in which the $S_{11}$ parameter is a minimum, and may determine the retrieved frequency as a resonant frequency.

FIG. 16 may indicate a frequency response characteristic 1600 of the $S_{21}$ parameter. In the frequency response characteristic 1600, a vertical axis is magnitude [dB] of the scattering parameter, and a horizontal axis is a frequency [GHz]. In the frequency response characteristic 1600, a frequency indicative of maximum magnitude may be a resonant frequency. For example, if the bio sensor monitors the $S_{21}$ parameter among scattering parameters, the bio sensor may search a target frequency range for a frequency in which the $S_{21}$ parameter is a maximum, and may determine the retrieved frequency as a resonant frequency.

FIG. 17 is a graph 1700 illustrating a resonant frequency change according to a change in relative dielectric constant. In the graph 1700, a vertical axis is the $S_{11}$ parameter [dB], and a horizontal axis is a frequency [GHz]. The graph 1700 may include a curve of the $S_{11}$ parameter according to a change in the frequency for each blood glucose value. The graphs illustrates that as the blood glucose value increases to 100 mg/dL, 150 mg/dL, 200 mg/dL, and 300 mg/dL, a resonant frequency in which the $S_{11}$ parameter is a minimum value is increased. A resonant frequency of the resonator assembly may be previously calculated and mapped for each concentration of the blood glucose. A relation between the concentration of blood glucose and the resonant frequency may be stored in a mapping table (e.g., a lookup table (LUT)). The bio sensor may determine, from the LUT, a concentration of a target analyte corresponding to a resonant frequency.

Figure 18:
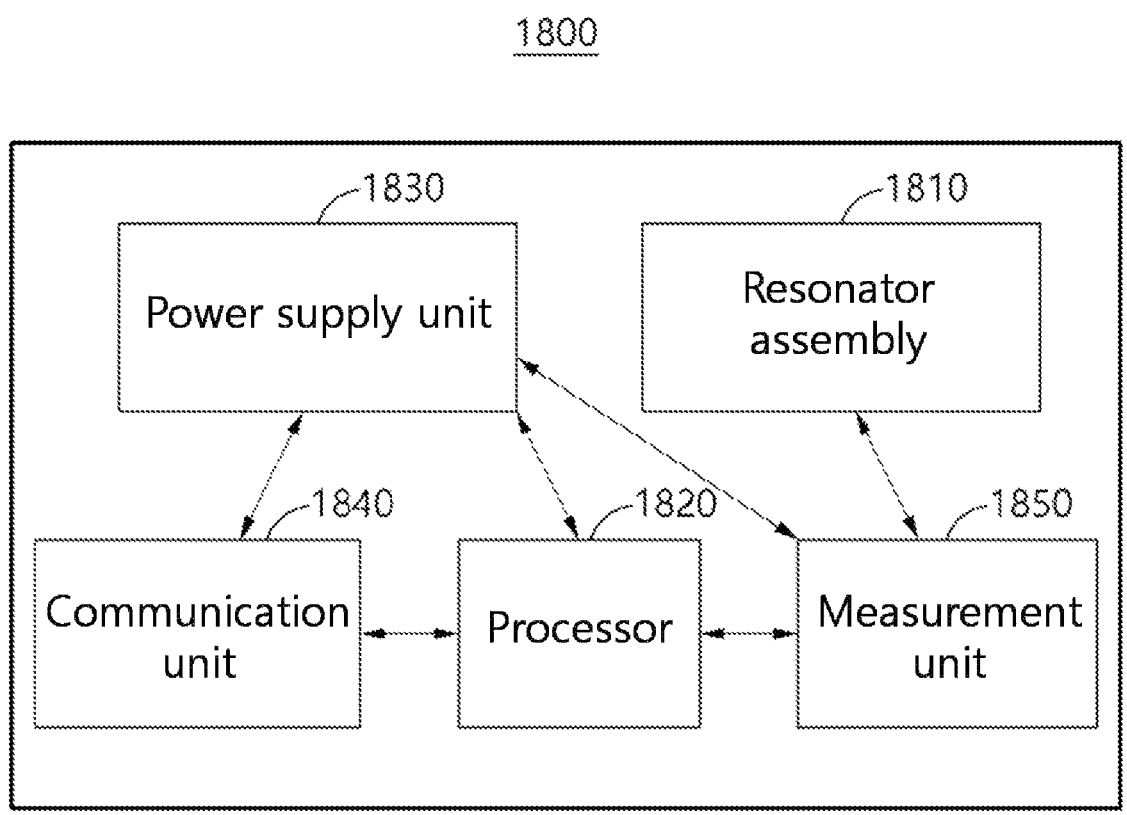
FIG. 18 is a block diagram illustrating a schematic configuration of the bio sensor using electromagnetic waves according to an embodiment.

FIG. 18 is a block diagram illustrating a schematic configuration of the bio sensor using electromagnetic waves according to an embodiment.

The bio sensor 1800 using electromagnetic waves according to an embodiment may include a resonator assembly 1810, a processor 1820, a power supply unit 1830, a communication unit 1840, and a measurement unit 1850.

The resonator assembly 1810 may include at least one feeding line which is disposed in the outskirts of a feeding area and may supply power to the feeding area and a pattern wire which is disposed along a pattern within the feeding area and may receive power from the feeding line through capacitive coupling. The resonator assembly 1810 has been described with reference to FIGS. 2 to 12, and a detailed description thereof is omitted.

The processor 1820 may obtain a parameter, associated with a resonant frequency of the resonator assembly 1810, as biometric data corresponding to a concentration of a target analyte present around the resonator assembly 1810, while a frequency of power supplied to the resonator assembly 1810 is swept. For example, the processor 1820 may collect a scattering parameter with respect to each frequency while a frequency of a signal supplied to the resonator assembly 1810 is swept within a target frequency range by the measurement unit 1850. The processor 1820 may determine a resonant frequency based on the collected scattering parameter. The processor 1820 may determine a concentration of the target analyte based on the resonant frequency.

The power supply unit 1830 may supply power to the processor 1820, the communication unit 1840, and the measurement unit 1850. The power supply unit 1830 may wirelessly receive power from an external device, and may supply power to each element within the bio sensor 1800. The power supply unit 1830 may include a battery, for example, and may charge the battery with power received from the external device. The power supply unit 1830 may supply power to the resonator assembly 1810, etc. through the measurement unit 1850 using power charged into the battery.

The communication unit 1840 may transmit biometric data to the external device and receive information from the external device. For example, the communication unit 1840 may establish wireless communication with the external device. The biometric data may include at least one of a scattering parameter, a resonant frequency, and a concentration of a target analyte.

The measurement unit 1850 may sweep a frequency of a signal supplied to the resonator assembly 1810 within a target frequency range, and may measure information related to a parameter of the resonator assembly 1810 during the frequency sweeping. For example, the measurement unit 1850 may measure electrical data of the resonator assembly 1810. The measurement unit 1850 may include a voltage sensor that measures a voltage of a port of the resonator assembly 1810. The measurement unit 1850 may sweep a frequency under the control of the processor 1820, and may supply the resonator assembly 1810 with a signal in a frequency swept within a target frequency range at sweeping frequency intervals determined by the processor 1820, for example, but the present disclosure is not limited thereto. The measurement unit 1850 may sweep a frequency through its own oscillation circuit structure even without the processor 1820.

Figure 19:
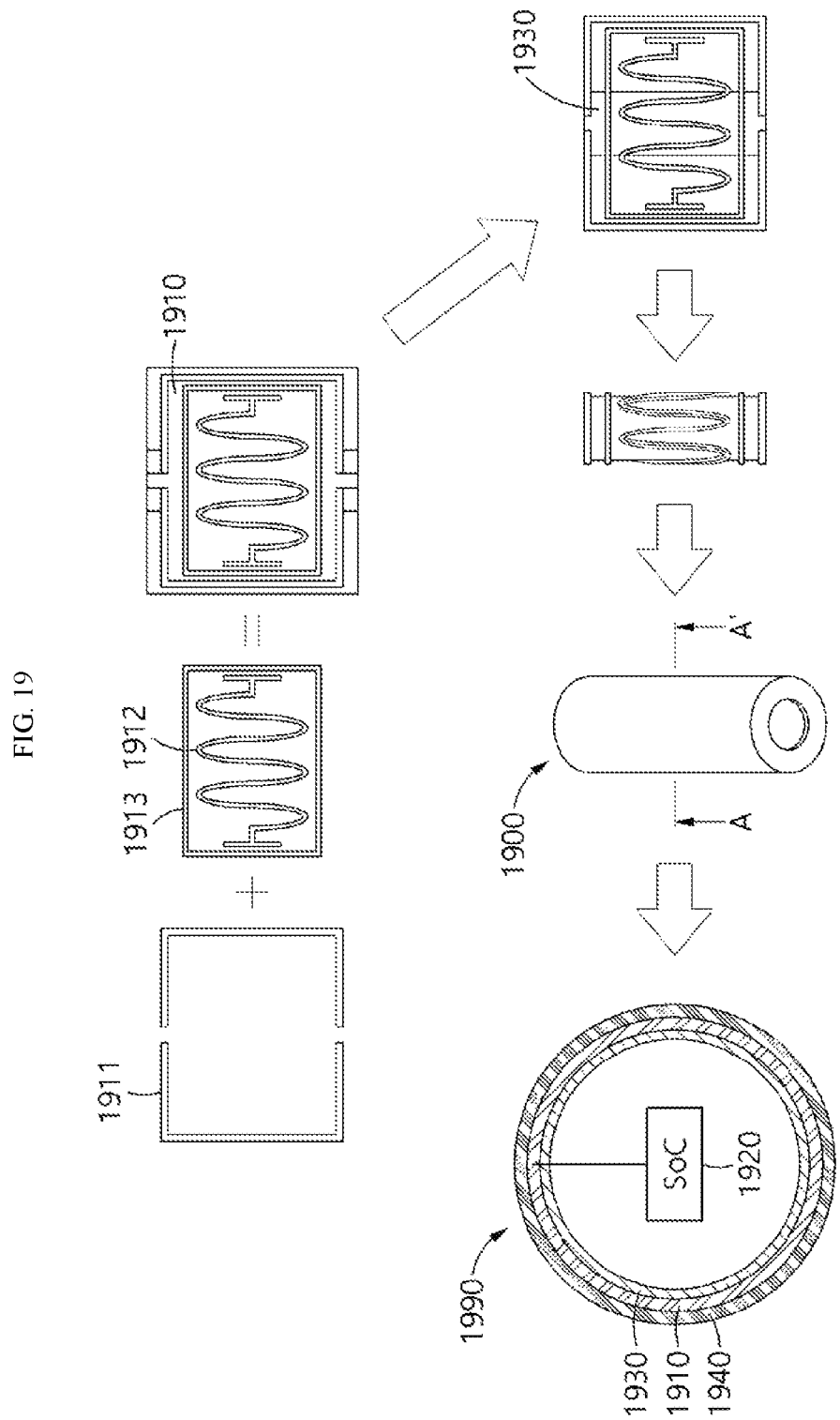
FIG. 19 illustrates an exemplary application of the bio sensor using electromagnetic waves according to an embodiment.

FIG. 19 illustrates an exemplary application of the bio sensor using electromagnetic waves according to an embodiment.

A feeding line 1911, a closed-loop wire 1913, and a pattern wire 1912 according to an embodiment may be disposed on one surface. A resonator assembly 1910 disposed on the one surface may be configured to surround a curved surface. For example, the one surface on which the resonator assembly 1901 is disposed may be a curved surface disposed along the side of a cylindrical support member 1940.

A cross section AA' of the cylindrical resonator assembly 1900 may be illustrated like a cross-sectional diagram 1990. Referring to the cross-sectional diagram 1990, the resonator assembly 1910 may be supported by a cylindrical support member 1930. An outer surface of the resonator assembly 1910 may be packed by a material suitable for a living body. The material suitable for a living body may be a poly methyl methacrylate (PMMA) material, for example, but the present disclosure is not limited thereto. The internal space of the cylindrical support member 1930 may accommodate a system on chip. The system on chip 1920 may indicate a single chip in which the processor 1820, the power supply unit 1830, the communication unit 1840, and the measurement unit 1850 described with reference to FIG. 18 have been implemented. However, this is illustrative, and the present disclosure is not limited thereto. The system on chip 1920 may be a chip in which at least one of the processor 1820, the power supply unit 1830, the communication unit 1840, and the measurement unit 1850 has been integrated and implemented.

As described above, although the embodiments have been described in connection with the limited embodiments and drawings, those skilled in the art may modify and change the embodiments in various ways from the description. For example, proper results may be achieved although the above descriptions are performed in order different from that of the described method and/or the aforementioned components, such as a system, a configuration, a device, and a circuit, are coupled or combined in a form different from that of the described method or replaced or substituted with other components or equivalents.

Accordingly, other implementations, other embodiments, and equivalents of the claims fall within the scope of the claims.

The invention claimed is:

1. A resonator assembly, comprising:
   at least one feeding line disposed on one surface along outskirts of a feeding area and capable of supplying power to the feeding area; and
   a pattern wire disposed on the one surface along a pattern within the feeding area and capable of receiving power from the feeding line through capacitive coupling,
   wherein the pattern wire comprises:
   a first coupling portion disposed adjacent to the at least one feeding line on the one surface to form capacitive coupling;
   a second coupling portion disposed adjacent to at least one of the feeding line, a closed-loop wire, and an additional pattern wire on the one surface to form capacitive coupling; and
   a connecting portion connecting the first coupling portion and the second coupling portion along the pattern on the one surface;
   wherein the connecting portion is disposed along the pattern in a sinusoidal shape.

2. The resonator assembly of claim 1, wherein a resonant frequency of the resonator assembly is different depending on a concentration of a target analyte present around the resonator assembly.

3. The resonator assembly of claim 1, further comprising a closed-loop wire disposed within the feeding area on the one surface,
   wherein the pattern wire is disposed in an internal area defined by a closed-loop wire and forms capacitive coupling with the feeding line via the closed-loop wire.

4. The resonator assembly of claim 3, wherein a part adjacent to a part of the feeding line in the closed-loop wire is isolated from a part of the feeding line and disposed in parallel to the part of the feeding line in a shape identical with a shape of the part of the feeding line.

5. The resonator assembly of claim 3, wherein the closed-loop wire is one shape of a polygon or a circular shape.

6. The resonator assembly of claim 1, wherein the connecting portion comprises a first part and a second part disposed on opposite sides in a virtual line which traverses the first coupling portion and the second coupling portion.

7. The resonator assembly of claim 6, wherein the first part and the second part are alternately disposed from the first coupling portion to the second coupling portion.

8. The resonator assembly of claim 1, wherein the first part and the second part have a point symmetry shape on the one surface.

9. The resonator assembly of claim 1, further comprising one or more additional pattern wires disposed on the one surface in a way to form capacitive coupling with at least one of the pattern wire and the feeding line.

10. The resonator assembly of claim 9, wherein the pattern wire and the one or more additional pattern wires form a meta surface (MTS).

11. The resonator assembly of claim 9, wherein the pattern wire and the one or more additional pattern wires are disposed in a form of patterns having an identical shape.

12. The resonator assembly of claim 9, further comprising a plurality of closed-loop wires individually surrounding the pattern wire and the one or more additional pattern wires, respectively, on the one surface.

13. The resonator assembly of claim 9, wherein the one or more additional pattern wires are isolated and disposed in one axis based on the pattern wire.

14. The resonator assembly of claim 1, wherein the one surface is a curved surface disposed on a side of a cylindrical support member.

15. The resonator assembly of claim 1, wherein the at least one feeding line comprises:
   a first feeding line disposed on the one surface and comprising ports connected to another element at both ends thereof; and
   a second feeding line isolated from the first feeding line on the one surface and disposed and comprising ports connected to another element at both ends thereof,
   wherein the feeding area is an area between the first feeding line and the second feeding line.

16. The resonator assembly of claim 1, wherein:
   the at least one feeding line is composed of a single feeding line comprising a port which receives power, and
   the feeding area is an area surrounded by the single feeding line.

* * * * *